(12) United States Patent
Bouwstra et al.

(10) Patent No.: US 7,459,431 B2
(45) Date of Patent: *Dec. 2, 2008

(54) RECOMBINANT GELATIN-LIKE PROTEINS FOR USE AS PLASMA EXPANDERS

(75) Inventors: Jan Bastiaan Bouwstra, Bilthoven (NL); Yuzo Toda, Goirle (NL)

(73) Assignee: Fuji Film Manufacturing Europe B.V., Tilburg (NL)

( * ) Notice: Subject to any disclaimer, the term of this patent is extended or adjusted under 35 U.S.C. 154(b) by 0 days.

This patent is subject to a terminal disclaimer.

(21) Appl. No.: 10/469,747

(22) PCT Filed: Mar. 6, 2002

(86) PCT No.: PCT/NL02/00147

§ 371 (c)(1), (2), (4) Date: Sep. 4, 2003

(87) PCT Pub. No.: WO02/070000

PCT Pub. Date: Sep. 12, 2002

(65) Prior Publication Data

US 2005/0119170 A1 Jun. 2, 2005

(30) Foreign Application Priority Data

Mar. 6, 2001 (EP) .................................. 01200837

(51) Int. Cl.
*A61K 38/16* (2006.01)
*C07K 14/00* (2006.01)

(52) U.S. Cl. ...................................... 514/12; 530/391.7
(58) Field of Classification Search ....................... None
See application file for complete search history.

(56) References Cited

U.S. PATENT DOCUMENTS 3,984,391 A * 10/1976 Nitschmann et al. ......... 530/354
2005/0101531 A1 * 5/2005 Bouwstra et al. .............. 514/12

FOREIGN PATENT DOCUMENTS

WO      WO 01/34646 A2 *    5/2001

OTHER PUBLICATIONS

Nahas, G. et al. Prog. Clin. Biol. Res. 19: 259-264 (1978).*
Haemaccel package insert (published Aug. 28, 1992).*
Wootton, J., "Non-globular domains in protein sequences: automated segmentation using complexity measures", Computers Chem. vol. 18, No. 3, pp. 269-285, 1994.*

* cited by examiner

*Primary Examiner*—Anand U Desai
(74) *Attorney, Agent, or Firm*—K&L Gates LLP

(57) ABSTRACT

The invention relates to compositions suitable for plasma substitution comprising as a plasma expander a recombinant gelatin-like protein. Characteristic is that the gelatin-like protein essentially is free of hydroxyproline. This absence of hydroxyproline prevents the composition from gelling and thus allows the use of high-molecular weight proteins in order to establish a suitable colloid osmotic pressure. Specific advantage of the gelatin-like proteins is that these avoid the risk of anaphylactic shock that exists in conjunction with the use of commercially available preparations.

20 Claims, 2 Drawing Sheets

RECOMBINANT GELATIN-LIKE PROTEINS FOR USE AS PLASMA EXPANDERS

FIELD OF THE INVENTION

The invention relates to the use of recombinant gelatin-like proteins—or polypeptides—as plasma expanders and to compositions suitable for plasma substitution comprising such a plasma expander.

BACKGROUND OF THE INVENTION

A well established application of gelatin is the use as a colloid in solutions as substitutes for plasma. Such plasma substitutes can be used for controlling circulating blood volume in the management of shock resulting from for instance hemorrhages or burns. Care should be taken that the gelatin solution is made sterile, pyrogen and antigen free, and as the result of the average molecular size, is capable of maintaining a desired colloid osmotic pressure. In order to maintain a colloid osmotic pressure that is sufficient enough to have a sufficient amount of blood circulating and establish an efficient enough blood pressure, the size of the gelatin molecules would be such that gelling becomes a problem.

To render gelatin suitable as a plasma expander, it has been chemically modified in such a way that gelability is drastically reduced. For this purpose it is known that gelatin can be simultaneously degraded and crosslinked, branched or intermolecular bridges can be formed from the gelatin molecules. Probably the most successful modification is the preparation of succinylated gelatin as described in U.S. Pat. No. 2,827,419. A commercial preparation based on succinylated gelatin is currently available, known as Gelufusine®. The gelatin that is used is isolated from bovine origin and has an average molecular weight of 30,000. Other commercially available modified gelatines are Geloplasma® ('poligelatin') and Gelifundol® ('oxipoligelatin').

A disadvantage of the presently used gelatin derivatives as colloidal additives in plasma substitution compositions is the occurrence of hypersensitivity reactions in subjects. In particular subjects having an allergy or an auto-immune disease, or for some other reason having an increased level of antibodies, in particular IgE antibodies, are at risk. A case of acute emergency in which the administration of plasma expanders is required is in subjects suffering from shock, more specific hypovolemic shock due to severe bleeding, excessive fluid loss or inadequate fluid uptake. In such a situation there is simply no time to assess possible risk factors, such as the presence of an allergy. If a subject is known to have an allergy, prophylactic administration of an antihistaminicum can be contemplated. However, in case of acute emergency, any kind of prophylactic treatment is uncalled for. The condition of immediate hypersensitivity, which can occur upon application of the presently used gelatin derivatives, is known as anaphylactic shock. This is a life-threatening condition where blood pressure is too low to sustain life, which in fact was the condition that should be counteracted by the plasma expander. Since a subject receiving the plasma expanders already suffers an acute trauma the condition of anaphylactic shock is most likely to be fatal.

Another disadvantage of the commercially used gelatin derivatives is the fact that the gelatin used is isolated from animal sources such as animal bone and hide, in particular it is derived from bovine sources. Disadvantages of this material are the presence of impurities and the fact that the nature of the composition is not clearly defined and thus not reproducible. This may impose additional screening to ensure that the derivatisation process results in a product with the desired properties and may require careful purification steps. An additional problem nowadays, especially in relation to gelatin isolated from bovine sources, is the risk of contamination of the gelatin with factors resposible for the occurence of Bovine Spongiform Encephalitis (BSE). For this reason the use of gelatin in blood substitution products may be prohibited. At present at least for one product, a modified gelatin of bovine origin, it is known that as a precautionary measure the product is no longer commercially available.

Another disadvantage of the commercially used gelatin derivatives is the fa that the preparation of the gelatin figments with the intended size does not result in fully homogeneous material but in a heterogeneous mixture of gelatin fragments around a targeted average molecular weight. The smaller fragments will leave the blood circulation system by an early (unwanted) clearance by which their contribution to a stable clinical pattern is absent and the nephrotic system is negatively imposed.

SUMMARY OF THE INVENTION

It is an object of the invention to provide alternative compositions suitable as plasma substitution comprising a plasma expander, which will reduce the occurrence of immunological reactions, in particular anaphylactic shock.

Surprisingly it has been found that recombinant gelatin-like proteins which are in essence free of hydroxyproline do not give rise to an immunological reaction with blood samples containing IgE antibodies.

Thus, compositions according to the invention can comprise a solution of saline in a physiologically acceptable concentration and a protein having a colloid osmotic function. The protein having a colloid osmotic function can be a recombinant gelatin-like protein which is in essence free of hydroxyproline. Preferably the recombinant gelatin-like protein is also free of hydroxylysine; in addition preferably it is also free of lysine.

The invention relates also to the use as a plasma expander of a recombinant gelatin-like protein which is in essence free of hydroxyproline. Preferably for this use the recombinant gelatin-like protein is also free of hydroxylysine; in addition preferably it is also free of lysine.

Less than 2% of the aminoacid residues in the gelatin-like protein can be hydroxyproline residues, preferably less than 1%. Less than 0.2% of the aminoacid residues in the gelatin-like protein can be hydroxylysine residues, preferably less than 0.1%. In compositions according to the invention, less than 2%, preferably less than 1% of the aminoacid residues in the gelatin-like protein can be lysine residues.

The recombinant gelatin-like protein can have a molecular weight of at least 10,000 Daltons, preferably at least 15,000 Daltons, more preferably at least 20,000 Daltons. The recombinant gelatin-like protein can have a molecular weight between about 30,000 Daltons and 80,000 Daltons.

Furthermore, the recombinant gelatin-like protein can be homodisperse. A composition embodying the invention can comprise two or more recombinant gelatin-like proteins each of which is homodisperse but has a different molecular weight.

A composition according to the invention can comprise one or more components in a physiologically acceptable concentration selected from $Mg^{2+}$, $K^+$, $Ca^{2+}$, $HPO_4^{2-}$, $H_2PO^{4-}$ and glucose.

Also, a composition according to the invention can comprise a buffering compound, preferably selected from HCO3- and lactate. Furthermore, a composition according to the invention can comprise a pharmacologically active compound. The pharmacologically active compound can be covalently attached to the gelatin-like protein.

The invention includes the use as a plasma expander of a recombinant gelatin-like protein which is in essence free of hydroxyproline, in essence free of hydroxylysine and/or in essence free of lysine.

DESCRIPTION OF THE INVENTION

According., to the invention a composition is provided comprising as a compound having a colloid osmotic function a recombinant gelatin-like protein which is in essence free of hydroxyproline.

Recombinant production of gelatin-like proteins in particular in a micro-organism allows reproducible production of proteins of constant composition without the risk of prion related health hazards.

In example 2 it is shown that in the case of two blood samples out of a panel of 60 samples obtained from subjects in which IgE antibodies in the samples are present, two tested commercial preparations display specific binding of the IgE to the gelatin derivative, whereas in all the samples the compositions according to the invention display no risk of a hypersensitivity reaction. If the subjects from which the two positively tested samples originated, when in need, were to receive the commercially available gelatin based plasma substitution compositions, said subjects would likely suffer anaphylactic shock.

A natural gelatin molecule in its primary amino acid sequence basically consists of repeats of Gly-Xaa-Yaa triplets, thus approximately one third of the total number of amino acids is a glycine. The molecular weight of gelatin is typically large, values of the molecular weight vary from 10,000 to 300,000 Daltons. The main faction of natural gelatin molecules has a molecular weight around 90,000 Daltons. The average molecular weight is higher than 90,000 Daltons.

Furthermore, characteristic for gelatin is the unusual high content of proline residues. Even more characteristic is that in natural gelatin a number of the proline residues is hydroxylated. Most prominent site of hydroxylation is the 4-position resulting in the presence in the gelatin molecule of the unusual amino acid 4-hydroxyproline. In a triplet 4-hydroxyproline is always found in the Yaa position. Very few proline residues are hydroxylated at the 3 position. In contrast with 4-hydroxyproline, 3-hydroxyproline is always found at the carboxyl side of a glycine residue, thus in the Xaa position in a triplet. Different enzymes are responsible for the formation of 3- or 4-hydroxyproline.

Based on known amino acid compositions, it is estimated that in a gelatin molecule derived from a mammal, approximately 22% of the amino acids are a proline or a hydroxyproline residue. However lower contents of proline and hydroxyproline are found in fish, in particular cold water fish. A rough estimate is that proline and hydroxyproline residues are present in approximately equal amounts, thus in a gelatin molecule derived from a mammal approximately 11% of the amino acids are prolines and approximately 11% are hydroxyprolines. As substantially all hydroxyproline is found in the Yaa position, it is estimated that approximately one third of all triplets in a gelatin molecule comprise a hydroxyproline. The presence of the hydroxyproline residues is responsible for the fact that a gelatin molecule in its secondary structure can adopt a helical conformation.

Furthermore, another amino acid present in natural gelatin that is found in very few other proteins is 5-hydroxylysine. Lysine residues modified in this way are always found in the Yaa position in a triplet.

Gelatin-like proteins for use according to the invention are understood as proteins in which at least 5% of the total number of amino acids is a proline residue. By this percentage the gelatin-like characteristics, for the purpose of this invention not being defined as the gelling property but as the absence of unpreferred 3-dimensional globular domains, is assured. Preferably in the gelatin-like protein at least 10%, more preferably at least 15% of the total number of amino acids is a proline residue. The lower the proline content of a protein the more the distribution of the proline residues in the protein becomes relevant. Thus in a protein in which 5% of the total number of amino acids is a proline residue, these residues are preferably evenly distributed. In designing a suitable protein the skilled person, for instance with the aid of computer modeling systems, will be able to design sequences comprising proline residues which will not give rise to globular domains. In order to prevent the formation of globular domains as a guideline the gelatin-like protein for use in the invention preferably should not comprise stretches of more than 20 amino acids without a proline residue.

A predominant feature of gelatins is the presence of Gly-Xaa-Yaa triplets. Such triplets are preferably also present in the gelatin-like proteins used in the invention. It is however possible to design a protein in which Gly-Xaa-Yaa triplets or stretches of Gly-Xaa-Yaa triplets are separated by one or more amino acids. In such a gelatin-like protein having 'interrupted' triplets or stretches of triplets the definition of gelatin-like characteristics given above is useful. In relation to a protein consisting completely of Gly-Xaa-Yaa triplets the definition given above of a gelatin-like protein for use in the invention can be described as a protein in which at least 15% of the triplets comprise a proline residue. Preferably such a gelatin-like protein does not comprise a stretch of more than 6 triplets without a proline residue. It is preferred a gelatin-like protein for use in the invention comprises stretches of at least 10, preferably at least 20, more preferably more than 30 consecutive repeats of Gly-Xaa-Yaa triplets.

In order to maintain a suitable colloid osmotic pressure in combination with a targeted clearance rate from the blood circulation system when administered to a subject, the molecular weight of a gelatin-like molecule for use according to the invention should be at least 10,000 Daltons, preferably more than 15,000 Daltons, more preferably more than 20,000 Daltons. Most preferably the molecular weight is between about 30,000 Daltons and 80,000 Daltons. The gelatin-like molecule for use according to the invention is in essence free of hydroxyproline residues, meaning that less than 2% of the amino acid residues in the gelatin-like protein are hydroxyproline residues, preferably less than 1%. Preferably it is in essence free of hydroxylysine residues, meaning that less than 0.2% of the amino acid residues in the gelatin-like protein are hydroxylysine residues, preferably less than 0.1%. Advantageously it is in essence also free of lysine residues, meaning that less than 2%, preferably less than 1% of the aminoacid residues in the gelatin-like protein are lysine residues.

The amount of hydroxyprolines, hydroxylysines and lysines can be determined by any standard amino acid analysis method like, for example, described in HP AminoQuant Series II, operators handbook, 1990, Hewlett-Packard GmbH, Federal Republic of Germany, Waldbronn Analytical Division, HP Part No. 01090-90025.

For a considerable number of subjects gelatin and gelatin derivatives are not considered to be immunogenic compounds. For instance this is evidenced by the existence of commercial plasma substitution products based on gelatin. The fact that the gelatin that is used is not human in origin appears to be no problem. Also the fact that such gelatins are chemically modified appears not to be a problem. A sufficient amount of subjects are potentially able to benefit from the presently common preparations, giving such preparations reason to exist.

There are however subjects, like those having allergies or auto-immune diseases, that cannot tolerate the commercial preparations for plasma substitution based on gelatin derivatives. Faced with this problem a first improvement could be to try to improve on the purification of the gelatin proteins. One approach is optimizing even further the isolation procedure of natural gelatin or optimizing the derivatization and subsequent purification procedure. Another possibility could lie in alternative sources or alternative production methods for gelatin. Having knowledge of the current biotechnological developments and the advance that is made with respect to recombinant production of gelatins and collagens it could be contemplated to follow such a route for reproducible production of proteins of constant composition.

As mentioned earlier, although gelatins appear not to be very immunogenic they can be lethal to subjects having an allergy or an auto-immune disease. When pursuing the approach of recombinant production of gelatins and bearing in mind that such gelatins should be even less immunogenic in human subjects than the presently used bovine derived gelatins, it is obvious to take up production of recombinant human gelatin. In addition it is obvious not to induce marked changes in the basic gelatin structure.

In contrast to these obvious possible solutions, suitable gelatin-like proteins for use according to the invention can be non-natural, or can be equivalent to natural occurring gelatins. Non-natural in this context means that the gelatin is derived from a synthetic gene. The most prominent difference of the gelatin-like proteins for use according to the invention is the absence of hydroxyproline residues compared to natural gelatin molecules. The presence of hydroxyproline residues in natural gelatin allows the molecule to adopt a helical conformation. The absence of hydroxyproline residues prevents the gelatin-like proteins from adopting such a conformation and prevents the gelatin-like molecule from gelling, even at low temperatures.

There is no prior art information on immunological or antigenic properties of gelatin-like proteins useful in the invention. The distinctiveness of the gelatin-like proteins for use according to the invention from natural gelatin, both chemically and conformationally, would dissuade the use of such a protein in pleura substitution compositions. Surprisingly however, gelatin-like proteins for use according to the invention show no immunogenic interaction with blood having increased amounts of IgE antibodies.

Gelatin-like proteins for use according to the invention are in essence free of hydroxyproline. This means that to a certain level of hydroxyproline residues is allowed. The level of hydroxyproline residues should be lower than the minimum level that is required to let a 5 weight % solution of the protein in isotonic saline at neutral pH gel at 5° C. This condition is met by for instance gelatin-like proteins in which less than 2% of the aminoacid residues are hydroxyproline residues.

In a further embodiment, the gelatin-like protein for use in the invention is in essence free of hydroxylysine. This is most efficiently achieved by avoiding the formation of hydroxylysine in yet a further embodiment in which the gelatin-like protein for use in the invention is in essence free of lysine. As mentioned above, hydroxylysine is rarely found in proteins. It could be possible that hydroxylysine or a particular sequence in which hydroxylysine is present, is involved in antigenic interactions. Antigenic interactions could be the result of the presence of the amino acids itself or could be the result of particular conformations the gelatin or gelatin derivative might adopt due to the presence of hydroxylysine.

The gelatin-like protein can be made de novo from a synthetic nucleic acid sequence. This allows tailor-made design of the protein. The designed synthetic nucleic acid sequence can be expressed in suitable micro-organisms using known recombinant techniques.

With respect to the design of gelatin-like proteins for use in the invention, several properties of the proteins are addressed. For instance it can be made sure specific amino acids, such as lysine, will not occur in the protein. Otherwise, as discussed below in particular with respect to lysine as well, it can be advantageous to introduce a definite number of a specific amino acid in the gelatin-like protein. Also the clearance speed of the gelatin-like proteins can be "designed-in" by the choice for a or size or a specific range of sizes of the gelatin-like proteins. In particular this could be advantageous in combination with known nephrotic system characteristics (measured by for instance the creatinine clearance pattern) of subjects to whom the gelatin-like proteins are administered. The size of the gelatin-like proteins is further of importance for the colloid osmotic pressure, as discussed below, it exercises. Yet further the iso-electric point (IEP) can be tuned by the composition of acidic and basic amino acid residues in the gelatin-like proteins.

In one embodiment the composition according to the invention comprises a gelatin-like protein which is homodiperse in nature. Homodisperse means of constant composition and molecular weight. Variations in composition that can occur due to the recombinant production process are allowed. In terms of molecular weight a useful definition of homodispersity would be that at least 90% of the total amount of gelatin-like protein in the composition has a molecular weight that lies within a range of plus or minus 10% around a selected molecular weight. The selected molecular weight depends on the desired colloid osmotic pressure and on the desired clearance rate from the blood circulation system. In another embodiment the composition according to the invention comprises two or more gelatin-like proteins each being homodiperse in nature but with different molecular weights. The difference in molecular weight results in a different clearance pattern from the circulating blood. Such a composition allows tuning of the plasma expanding activity of the composition over prolonged periods of time.

The starting point for the gelatin-like protein for use in the invention can also be an isolated gene encoding a naturally occurring gelatin molecule, which is processed further by recombinant means. Preferably the gelatin-like protein used according to the invention resembles a human native amino acid sequence with this difference that in essence hydroxyproline residues are absent.

The gelatin-like proteins for use according to the invention can be produced by recombinant methods as disclosed in U.S. Pat. No. 6,150,081 and EP-A-1014176. For enablement of the production and purification of gelatin-like proteins that can be suitably used in composition according to the invention specific reference is made to the examples in U.S. Pat. No. 6,150,081 and EP-A-10 14176. Thus the gelatin-like proteins can be produced by expression of nucleic acid sequence encoding such polypeptide by a suitable micro-organism. The process can suitably be carried out with a fungal cell or a yeast cell. Suitably the host cell is a high expression host cells like *Hansenula, Trichoderma, Aspergillus, Penicillium, Neurospora or Pichia*. Fungal and yeast cells are preferred to bacteria as they are less susceptible to improper expression of repetitive sequences. Most preferably the host will not have a high level of proteases that attack the collagen structure expressed. In this respect *Pichia* offers an example of a very suitable expression system. As disclosed in U.S. Pat. No. 6,150,081 and EP-A-1014176 specifically *Pichia pastoris* is used as expression system. Preferably the micro-organism is free of active post-translational processing mechanism such as in particular hydroxylation of proline and also hydroxylation of lysine. The host to be used does not require the presence of a gene for expression of prolyl-4-hydroxylase. Preferably the host also does not require the presence of lysylhydroxylase. Generally the recombinant production method will result in proteins comprising natural amino acids, i. e. L-amino acids. The presence of D-amino acids as a result of isomerisation processes that can occur naturally is allowed. Less than 1% of the amino acids is in the D-form. The selection of a suitable host cell from known industrial enzyme producing fungal host cells specifically yeast cells on the basis of the required parameters described herein rendering the host cell suitable for expression of recombinant gelatin-like proteins suitable in compositions according to the invention in combination with knowledge regarding the host cells and the sequence to be expressed will be possible by a person skilled in the art.

When produced by recombinant means, especially by expression of recombinant genes in yeasts, the proteins for use according to the invention preferably do not contain cysteine or another mercapto amino acid, nor do they contain a combination of methionine and arginine in 1-4 position (Met-Xay-Xaz-Arg), as such a sequence is sensitive to enzymatic proteolysis.

It may be noted that the proteins for use according to the invention can also be partly or wholly produced by methods other than DNA expression, e.g. by chemical protein synthesis; in that case, they may also contain non-natural amino acids.

In order to obtain the composition of the invention the gelatin-like protein is dissolved in saline in a physiologically acceptable concentration at physiological pH. Saline is a solution of $Na^+$ and $Cl^-$ ions in water. Since it is highly likely that plasma substitution compositions are administered in great volumina, care should be taken that dilution effects do not disturb electrolyte balances. When preparing compositions according to the invention the skilled person will be able to apply appropriate concentrations of $Na^+$ and $Cl^-$ ions. Workable margins would be 120-170 mmol/l for $Na^+$ and 90-140 mmol/l for $Cl^-$. If so desired the composition according to the invention could comprise one or more additional components normally found in blood. For instance a composition according the invention comprises one or more components in a physiologically acceptable concentration selected from $Mg^{2+}$, $K^+$, $Ca^{2+}$, $HPO_4^{2-}$, $H_2PO_4^-$ and glucose. The skilled person will be able to determine what is a physiologically acceptable concentration for each component. Suitably, a composition according to the invention also comprises a buffering compound, preferably selected from the group consisting of $HCO_3^-$ and lactate. The skilled person will be able to determine the appropriate amount of buffer in order to maintain the composition at a physiologically acceptable pH.

It is preferred the composition according to the invention is approximately isotonic or iso-osmotic with blood of human subjects, therefore the composition has an osmolarity preferably in the range from 270-300 mOsm.

The purpose of the gelatin-like proteins is to maintain an appropriate colloid osmotic pressure in order to keep a sufficient amount of blood volume circulating. The non-gelling property of the proteins for use according to the invention has the advantage that macromolecules of considerable size can be used which will not be rapidly cleared from the system. In order to be effective as plasma expander the gelatin-like compounds should have a molecular weight of at least 10,000 Daltons, preferably at least 15,000 Daltons, even more preferable at least 20,000 Daltons. Most preferably the molecular weight is between about 30,000 Daltons and 80,000 Daltons. According to the invention it is possible to apply even much larger gelatin-like proteins in case this is preferred depending on the desired colloid osmotic pressure and/or the desired clearance rate from the blood circulation system. Compositions comprising gelatin-like proteins of high molecular weight can be applied without the risk of gelling or of a too high viscosity. It does not seem likely however, that gelatin-like proteins having a molecular weight of higher than 100,000 Daltons can be suitably applied in compositions according to the invention.

The composition of the invention comprises an amount of gelatin-like proteins which exerts an osmotic pressure comparable to or slightly exceeding the osmotic pressure exerted by human serum albumin in blood. Determining the colloid osmotic pressure of a composition is a routine measurement for the skilled person, for instance by using a commercially available membrane osmometer equipped with a suitable semi-permeable membrane, for instance with a cut-off of 20,000 Daltons. The skilled person will be able to determine the correct amount of gelatin-like protein suited for the desired osmotic pressure. Usually the amount of gelatin-like protein that can be applied lies in the range from 2-8 weight %.

If so desired, it is possible to introduce simultaneously with the plasma substitution composition of the invention a pharmacologically active compound. For instance it may be advantageous to simultaneously introduce medicaments involved in the blood clotting process. In particular such a composition could be of use in the application of a plasma expander during surgery or preoperative dilution of blood. Thus in another embodiment the composition according to the invention comprises a pharmacologically active compound.

Making use of the advantageous property of the gelatin-like protein that it has a sustained circulation time in plasma it is particularly envisaged to covalently attach pharmaceutically active compounds to the gelatin-like protein. In a further embodiment the composition according to the invention comprises a pharmaceutically active compound which is covalently attached to the gelatin-like protein.

Covalent attachment of a pharmaceutically active compound to a protein is routine practice for an ordinary skilled organic chemist. For instance coupling of a carboxyl function in a drug to an amino group of a lysine in a protein can be achieved by converting the carboxyl group in its activated ester using DCC, or EDC, and NHS, which reacts with the free amine.

As in a protein lysine residues are the residues of choice for the covalent attachment of other molecules, it is for this purpose not desired to have a protein that is in essence free of lysine residues. In contrast, lysine residues should be present and preferably the number of lysine residues present is known, for this allows an estimation of how many pharmacologically active compounds are coupled to a protein and thus allows appropriate dosage of the medicament. The design of synthetic nucleic acid sequences de novo now offers the advantageous possibility to introduce a specific amount of lysine residues and thus the production of well defined gelatin-like proteins bearing pharmaceutically active compounds. A distinct correlation between clearance time of the protein and dosage of the medicament can be made.

After administration the coupled medicament will not diffuse from the circulating blood into the interstitium. This is a specific advantage for medicaments which should function intravascularly. Unwanted side effects by diffusion of the medicament into the interstitial fluid throughout a subject are avoided. Also medicaments having an intravascular as well as an extravascular activity profile could benefit from the focus on the intravascular mode of action.

Clearance by liver and kidney will be kept to a minimum ensuring a more constant plasma level of the medicament. Half-lives of medicaments coupled to gelatin-like proteins will be increased.

Examples of medicaments which are administered intravascularly and which are suitable for coupling to the protein used in the invention are medicaments involved in intervening blood clotting, vasodilatation, function of erythrocytes, thrombocytes and leukocytes, thrombosis, immune responses, blood levels of messenger molecules such as hormones. Specific examples are heparin, beta-blockers, blood pressure regulators such as angiotensin antagonists and antibiotics.

It should be understood that modification of the gelatin-like proteins for use in compositions according to the invention is not restricted to the coupling of pharmacologically active compounds. To improve the properties other modifications after the gelatin-like protein has been recombinantly produced and isolated are possible. For instance modifications to influence the iso-electric point or the solubility or another relevant property can be advantageous. Care should be taken that such a modification does not introduce elements that are likely to induce an immunogenic or antigenic reaction.

EXAMPLES

Example 1

Recombinant Collagen-like Peptide

General Molecular-biological Techniques

Figure 1:
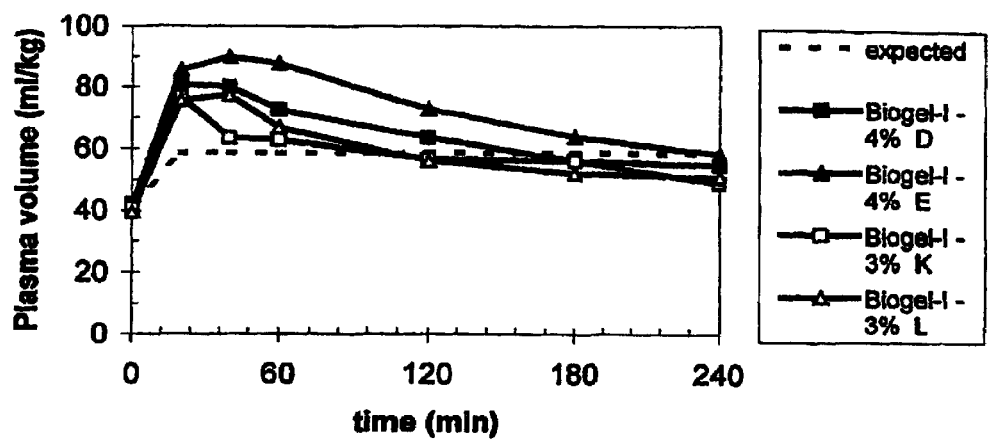
FIG. 1: Plasma volume expansion as a function of time after infusion of biogel-I.

Cloning procedures were performed essentially according to Maniatis et al. [Maniatis T., Fritsch, E. F. & Sambrook, J. (1982) Molecular cloning: A laboratory manual. Cold Spring Harbor Laboratory, Cold Spring Harbor, N.Y.]. Plasmid DNA was isolated using Wizard Plus SV miniprep, or Qiagen miniprep systems. DNA was isolated from agarose gels using the QIAquick Gel Exaction Kit (Qiagen). All enzymes used were from Amersham Pharmacia Biotech unless otherwise stated and were used according to the recommendations of the manufacturer. AU procedures involving the handling and transformation of *Pichia pastoris* were essentially performed according to the manual of the *Pichia* Expression Kit (Invitrogen) [Manual of the *Pichia* Expression Kit Version E (Invitrogen, San Diego, Calif., USA)].

Construction of pPIC9-H1

A synthetic gene encoding a hydrophilic gelatin with six histidine residues (referred to hereafter as "Biogel-II") was designed to have the codon usage of *Pichia pastoris* highly expressed genes (Sreekrishna, K. and Kropp, K. E. (1996) *Pichia pastoris*, Wolf, K. (Ed), *Non conventional yeasts in biotechnology. A handbook*, Springer-Verlag, pp. 6/203-6/253).

Two separate PCR reactions were performed, using the following oligonucleotides:

1. 1 pmol OVL-PA-FW, 1 pmol OVL-PA-RV, 50 pmols HLP-PA-FW and 50 pmols HLP-PA-RV.
2. 1 pmol OVL-PB-FW, 1 pmol OVL-PB-RV, 50 pmols HLP-PB-FW and 50 pmols HLP-PB-RV.

Oligonucleotide sequences were as follows:

```
HLP-PA-FW:
5'-GCGCTCGAGA AAAGAGAGGC TGAAGC-3'
(SEQ ID NO: 1)

OVL-PA-FW:
5'-GCGCTCGAGA AAAGAGAGGC TGAAGCTGGT

CCACCCGGTG AGCCAGGTAA CCCAGGATCT CCTGGTAACC

AAGGACAGCC CGGTAACAAG GGTTCTCCAG GTAATCCCA-3'
(SEQ ID NO: 2)

OVL-PA-RV:
5'-TGAGAACCTT GTGGACCGTT GGAACCTGGC TCACCAGGTT

GTCCGTTCTG ACCAGGTTGA CCAGGTTGAC CTTCGTTTCC

TGGTTGACCT GGATTACCTG GAGAACCCTT-3'
(SEQ ID NO: 3)

HLP-PA-RV:
5'-TGAGAACCTT GTGGACCGTT GGAA-3'
(SEQ ID NO: 4)

HLP-PB-FW:
5'-TTCCAACGGT CCACAAGGTT CTCA-3'
(SEQ ID NO: 5)

OVL-PB-FW:
5'-TTCCAACGGT CCACAAGGTT CTCAGGGTAA

CCCTGGAAAG AATGGTCAAC CTGGATCCCC AGGTTCACAA

GGCTCTCCAG GTAACCAAGG TTCCCCTGGT CAGCCAGGTA

ACCCT-3'
(SEQ ID NO: 6)

OVL-PB-RV:
5'-GCGTCTGCAG TACGAATTCT ATTAGCCACC GGCTGGACCC

TGGTTTCCTG GTTTACCTTG TTCACCTGGT TGACCAGGGT

TACCTGGCTG ACCAGGGGAA CCTTGGTT-3'
(SEQ ID NO: 7)

HLP-PB-RV:
5'-GCGTCTGCAG TACGAATTCT ATTAGC-3'
(SEQ ID NO: 8)
```

The 50 μl PCR reactions were performed in a GeneAmp 9700 (Perkin-Elmer) and contained 0.2 mM dNTP's Pharmacia), 1× Pwo buffer (Eurogentec) and 1.25 U Pwo polymerase (Eurogentec). Reaction 1 involved 18 cycles consisting of 15 seconds at 94° C. and 15 seconds at 72° C. Reaction 2 involved a touchdown PCR, whereby each cycle consisted of 15 seconds at 94° C., 15 seconds at the annealing temperature and 15 seconds at 72° C. The annealing temperature was lowered from 72° C. to 68° C. in the first 5 cycles, after which 20 additional cycles at an annealing temperature of 67° C. were performed.

The PCR products were isolated from agarose gel. 0.3 pmols of each fragment and 50 pmols of the outer primers HLP-PA-FW and HLP-PB-RV were subjected to overlap extension PCR. 25 cycles consisting of 15 seconds at 94° C., 15 seconds at 67° C. and 15 seconds at 72° C. were performed. The resulting 0.3 kb PCR fragment was digested with XhoI/EcoRI and inserted in cloning vector pMTL23. An errorless clone (referred to hereafter as "pMTL23-P") was selected by verification of the sequence by automated DNA sequencing.

An additional PCR reaction was performed using the following oligonucleotides: 1 pmol OVL-H-FW, 1 pmol OVL-H-RV, 50 pmols HLP-H-FW and 50 pmols HLP-H-RV.

Oligonucleotide sequences were as follows:

```
HLP-H-FW:
5'-CCACCCGGTG AGCCAGGA-3'
(SEQ ID NO: 9)

OVL-H-FW:
5'-CCACCCGGTG AGCCAGGAAA CCCTGGTCAC CACGGTAACC

AAGGACAGCC AGGTAACGAA GGTCAACCAG GTCAGGAAGG

TAATCCTGGA AACGAGGGTC AT-3'
(SEQ ID NO: 10)

OVL-H-RV:
5'-GCCACCGQCT GGACCTTGGT TACCGTGGTG TCCCTGCTCA

CCAGGTTGAC CTGGTTGACC CTCGTTTCCA GGTTGACCGT

GATGACCCTC GTTTCCAGGA TT-3'
(SEQ ID NO: 11)

HLP-H-RV:
5'-GCCACCGGCT GGACCTTG-3'
(SEQ ID NO: 12)
```

The 50 μl PCR reactions were performed in a GeneAmp 9700 (Perkin-Elmer) and contained the oligos indicated above and 25 μl of High Fidelity PCR Master (Roche). The reaction involved 18 cycles consisting of 15 seconds at 94° C., 15 seconds at 60° C. and 15 seconds at 72° C. The 0.18 kb PCR product was isolated from agarose gel and T/A cloned into vector pGEM-T Easy (Promega). An errorless clone was selected by verification of the sequence by automated DNA sequencing. The vector was then digested with DraIII/Van91I. The resulting 0.18 kb fragment was isolated from agarose gel and cloned into Van91I digested, dephosporylated pMTL23-P. The resulting vector was cut with EcoRI/XhoI, after which the insert was cloned into EcoRI/XhoI digested *P. pastoris* expression vector pPIC9, to yield vector pPIC9-H1.

The Encoded Amino Acid Sequence of the Mature (Processed) Biogel II is as Follows (SEQ ID NO: 13):

```
  1 G P P G E P G N P G S P G N Q G Q P G N K G S P G N P G Q P
 31 G N E G Q P G Q P G Q N G Q P G E P G S N Q P Q G S Q G N P
 61 G K N G Q P G S P G S Q G S P G N Q G S P G Q P G N P G Q P
 91 G E Q G K P G N Q G P A G E P G N P G H H G N Q G Q P G N E
121 G Q P G Q E G N P G N E G H H G Q P G N E G Q P G Q P G E Q
151 G H H G N Q G P A G G
```

Molecular weight: 15.1 kDa, isoelectric point: 5.1.

Example 2

Radio Allergen Sorbent Test (RAS Test or RAST)

In order to demonstrate the presence of IgE antibodies against certain allergens or proteins the RAS test is used. For a detailed description of the RAS test reference is made to Aalberse et al. J. Allergy Clin. Immunol., 1981, vol. 68: 356-364.

The compositions which contain gelatines that are tested are:

Gelofusine®, Gelifundol®, Composition containing Biogel-I, Composition containing Biogel-II and Composition containing Biogel-III Gelofusine® (modified gelatin 40 g/l $Na^+$ 154 mmol/l, $Cl^-$ 125 mmol/l) and Gelifundol® (modified gelatin 55 g/l, $Na^+$ 145 mmol/l, $Cl^-$ 100 mmol/l, NaEDTA 0.19 g/l, $Ca^{2+}$ 0.5 mmol/l, $HCO_3^-$ 30 mmol/l) were used as commercially obtained.

Biogel-I and Biogel-III are described in U.S. Pat. No. 6,150,081, FIG. 3 and columns 29-30 (as SEQ ID NO: 33 and SEQ ID NO: 34 respectively). Compositions comprising 55 g/l gelatin-like proteins Biogel-I, Biogel-II, and Biogel-III in PBS ($Na^+$ 164 mmol/l, $Cl^-$ 140 mmol/l, $HPO_4^-$ 10.9 mmol/l, $H_2PO_4^{2-}$ 1.8 mmol/l were prepared.

Sera of subjects which are known to have an allergy against specific foodstuffs were tested. The sera were selected on the known presence of IgE antibodies against foodstuff, in particular against beef, pork and egg. Subjects having IgE antibodies against these foodstuffs possibly also have IgE antibodies against gelatin.

In addition 49 plasma samples obtained from plasmafereses, selected on the presence of IgE antibodies against known allergies, were tested.

The gelatin derivative or gelatin-like protein is conjugated to CNBr-activated Sepharose beads (Amersham Pharmacia Biotech, Uppsala, Sweden) (approximately 1 μg protein per mg beads) following a standard conjugation protocol according to the manufacturer's instructions.

Using a buffer containing Human Serum Albumin the concentration is adjusted to 2 mg beads per ml.

250 μl Sepharose beads conjugated to a gelatin derivative or a gelatin-like protein are incubated overnight at room temperature with 50 W serum or plasma sample.

The beads are washed 4 times to remove excess serum or plasma and resuspended in 250 µl medium.

The beads are incubated overnight at room temperature with 50 µl anti-human IgE antibody labeled with $^{125}$I. The labeled IgE antibody is prepared following a standard procedure using chloramine T.

The beads are washed 4 times to remove excess $^{125}$I labeled anti-human IgE antibody. The reactivity in the samples is counted (with positive and negative controls). The presence of reactivity in a sample demonstrates binding of IgE in a serum or plasma to the gelatin derivative or gelatin-like protein and thus the risk of the occurrence of a hypersensitivity reaction.

Results

|  | Gelofusine ® | Gelifundol ® | Biogel-I | Biogel-II | Biogel-III |
|---|---|---|---|---|---|
| Serum 3093 | ++ | ++ | -- | -- | -- |
| Serum PF 175 | ++ | ++ | -- | -- | -- |
| Other sera | -- | -- | -- | -- | -- |

++ = specific immune reaction
-- = no immune reaction

In a control experiment the samples tested positive are pre-incubated with Gelofusine® or Gelifundol®. After pre-incubation, in the RAS test no radioactivity is found. The immunological reaction is specific for the gelatin derivatives used.

Preclinical Evaluation of Gelatin Solutions in Rats

In a preclinical evaluation of recombinant gelatin solutions in rats the following is addressed:

the capacity to expand the vascular volume (primary pharmacologic property)

the distribution, plasma half-life and excretion through the kidneys (pharmacokinetics)

Filling of the vascular system is related to the oncotic activity in vivo. Within limits, the amount of macromolecules infused determines the magnitude of the effect and not the concentration in the infused solution. The oncotic activity can therefore be determined by studying the hemodilution by a certain dose of gelatin. The accuracy will be better when different doses are applied. In practice, to obtain good measurable effects, for example, 20 ml/kg body weight (about 30% of the blood volume) can be withdrawn and replaced by the same volume of solutions with different concentrations of gelatin (around the estimated iso-oncotic concentration). The in vivo iso-oncotic concentration can be determined by comparing the actual effects on the red blood cell count with the expected effects.

When the macromolecules are cleared from the circulation the plasma volume will decrease, leading to an increase in red blood cell count or hematocryt. Therefore, measuring the changes in the red blood cell count and the gelatin plasma concentration in time will reveal the duration of the effect and the half-life of gelatin in the circulation. When different doses are applied it will become clear whether or not the half-life is dose dependent within the range of clinically relevant doses. Relatively small macromolucules (<30 kD, depending on charge and shape) may be cleared by the kidneys. Kidney excretion can be determined by collecting urine and measuring the gelatin concentration. When large amounts of gelatin are excreted, kidney tubuli may become blocked by precipitation of gelatin in kidney tubuli. This can be studied by light microscopy.

Constituents of the gelatin solutions, especially impurities from yeast, may induce inflammatory responses. This may, amongst others, lead to vasoactivity and/or activation of neutrophils.

Because the half-life is probably in the order of hours, a 4 hour duration seems to be sufficient for initial experiments. This means that the whole experiment can be done under anesthesia, which facilitates blood pressure measurement and blood sampling and minimizes discomfort for the rats.

The iso-oncotic activity can be determined without measuring plasma concentrations, but for determination of the clearance an assay for measuring gelatin in plasma and urine should be available. Alternatively, labeled gelatin could be used, with the drawback that labeling may change the properties.

Protocol:

Animal Data

Species: Rat

Strain/Sex: Wistar HsdCpb:WU, female

Procedures

1. Administration of Test Solutions

Withdrawal of blood: 20 ml/kg in 10 minutes

Infusion of gelatin solution: 20 ml/kg (4-6 ml) in 10 minutes

2. Blood and Urine Samples

Blood: 0.2 to 1.5 ml blood samples were collected from the venous cannula into syringe and rapidly transferred into EDTA-containing polypropylene vials at t=0, 60, 120 and 240 min.

Urine was collected into a preweighted vial. The volume was determined by weighing.

3. Duration of the Experiment

The experiments were terminated 240 minutes after administration of the test solution by giving a lethal dose of pentobarbital.

Test Control/Comparison Solution

| TEST/CONTROL/COMPARISON SOULTION | |
|---|---|
| Test solution 1 | recombinant rat gelatin, 36 kD Biogel-I |
| identity | Biogel-I 36 kD |
| supplier | Fuji |
| formulation | freeze dried |
| remarks | reconstituted with 0.9% NaCl at either 3 or 4 g/100 ml and stored at 4° C. until adminstration (for less than 1 week) |
| Control solution | saline |
| identity | 0.9% (w/v) NaCl |
| supplier | NPBI, Emmer-Compascuum, The Netherlands |
| formulation | sterile fuid for iv administration |
| remarks | |
| Comparison solution 1 | human albumin |
| identity | Cealb |
| supplier | CLB |
| formulation | solution for iv infusion, 20 g/100 ml |
| remarks | stored at 4° C., diluted with saline to 5 g/100 mL |

-continued

| TEST/CONTROL/COMPARISON SOULTION | |
|---|---|
| Comparison solution 2 | modified bovine gelatin |
| identity | Gelifundol |
| supplier | Biotest Pharma GmbH |
| formulation | solution, 5.5 g/100 ml |
| remarks | stored at 4° C., diluted with saline to 4 g/100 mL |

Laboratory Investigation a) Hematocrit was measured by centrifugation of blood in glass capillaries at 10,000 g for 5 min.
b) Red Blood cell count was done with an electronic cell counter (model ZF; Coulter Electronics)
c) Measurement of gelatin concentrations Gelatin conc were determined using reversed phase chromatography and detection at 220 nm Calculations The hematocrit at each time point is calculated from the rbc count at that time point, the rbc count at t=0 and the hematocrit at t=0.
The expected (hypothetical) volumina are calculated as follows:
i) expected blood volume (BV) is calculated assuming that no fluid shifts occur:
at t=0 in ml: 65 (ml/kg)* body weight (kg)
at t≧20: BV t=0−withdrawn volume+infused volume
ii) expected plasma volume (PV) is calculated in ml assuming that no fluid shifts occur and that the body hematocrit is equal to that in the peripheral blood:
at t=0 in ml: BV t=0* (1-hct t=0)
at t≧20: PV t=0−withdrawn plasma+infused volume
iii) expected hematocrit is calculated as (BV-PV)/BV
The real volumes are estimated as follows:
i) estimated real BV at t=0 as expected thereafter estimated from the ratio between the expected and the observed hematocrit:
at t=0 in ml: 65 (ml/kg)*body weight (kg)
at t≧20: BV expect*exp hct/obs hct
ii) estimated real PV at t=0 as expected thereafter estimated from calculated real BV and the observed hematocrit:
at t=0 in ml: BVt=0* (1-hct t=0)
at t≧20: estimated real BV* (1-hct)
The volume expansion by the infused test solution at t=60 was estimated from the infused volume and the difference between the estimated real plasma volume and the expected plasma volume:
i) volume expansion at t=60: infused volume−expected PVt=60+estimated real PVt=60
ii) volume expansion per g colloid (ml/g)

Results and Discussion

Expansion of Plasma Volume

FIG. 1 shows that withdrawal of blood and subsequent saline infusion resulted in an initial decrease of the hematocrit to about the expected value. However, thereafter hematocrite rose to substantially higher values. After 5% Albumin infusion the hematocrit values remained below that expected throughout the observation period. Infusion of Saline, without oncotic activity, resulted in hypovolemia in this model, whereas 5% Albumin induced sustained hypervolemia, which means that it is hyperoncotic for the rats. The volume expansion induced by the infusion of 30 ml/kg of infusate was calculated from the hematocrit changes. For saline this was 17-18 ml/kg, for 5% Albumin 40-44 ml/kg, both 1 hour after infusion. For albumin, this means an expansion of 27-30 ml per gram albumin in this model.

Biogel-I was hyperoncotic at a concentration of 4 g/10 ml (FIG. 1), there was clear hypervolemia during 2 to 3 hours The plasma expansion was 44-59 me/kg after infusion of 30 ml/kg, 3 g/100 ml appeared to be close to the isoncotic concentration, the plasma expansion 35-44 ml/kg. Overall, the volume expansion after 1 hour was 43 +/−6 (mean & SD) ml per gram of Biogel-I.

Figure 2:
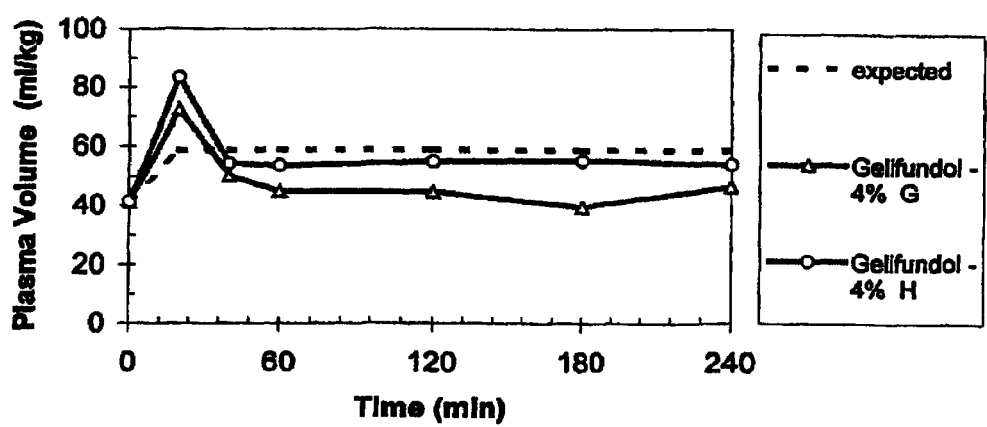
FIG. 2: Plasma volume expansion as a function of time after infusion of Gelifundol.

Gelifundol 4 g/100 ml had a very short volume effect (FIG. 2). The volume expansion after 1 hour was 17 and 25 ml/kg for an infused volume of 30 ml/kg, which is hardly more than saline. The volume expansion after 1 hour was 14-21 ml per gram colloid.

Figure 3:
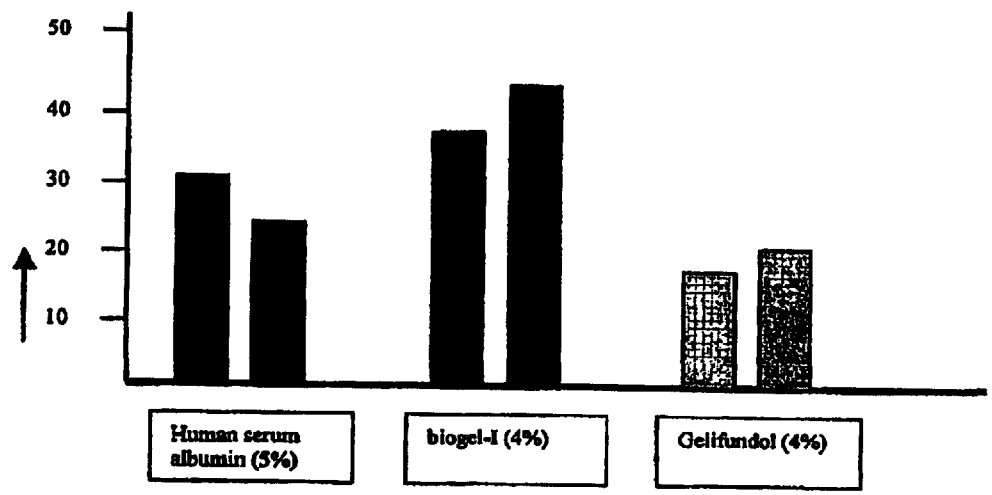
FIG. 3: Volume expansion by infused colloid at t=60 minutes.

FIG. 3 compares the onctoic effect as volume expansion of Biogel-I to Gelifundol and HSA, showing the improved short tern volume expansion of biogel-I.

These results show that Biogel-I is a very effective plasma expander both in short term- and long term volume expansion. The in vivo oncotic effect was, on a weight base, about 50% higher than that of human albumin. In comparison, Gelifundol had a minimal and very short-lasting oncotic effect in the rat model.

B. Plasma Clearance

Figure 4:
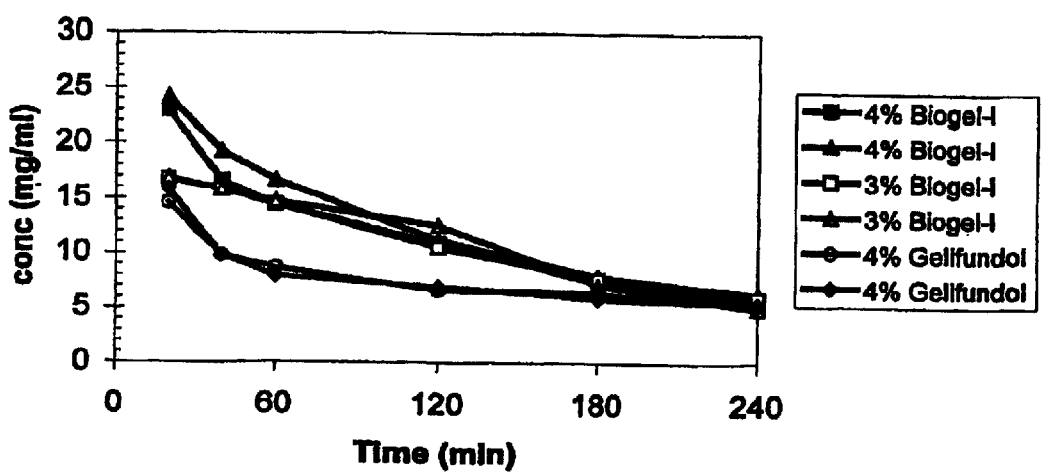
FIG. 4: Gelatin plasma concentration as a function of time after infusion of Biogel-I or Gelifundol.

FIG. 4 shows the gelatin plasma concentrations after infusion of 3 g/100 ml and 4 g/100 ml Biogel-I and 4 g/100 ml Gelifundol.

For Biogel-I, the initial distribution volume at t=20 min was 49-54 ml/kg independent of the infused concentration. This corresponds more or less to the expected plasma volume, indicating intravascular distribution without binding. The concentration then slowly decreased to 20-30% of the initial value after 4 hours. From these curves an apparent plasma half-life was calculated for Biogel-I of 87 +/−13 min (mean & SD). It should be noted that in the 3 hour observation period also distribution occurs into the extravascular space. There was no excretion detected into the urine.

Gelifundol had an initial distribution volume of 75-82 ml, suggesting that part of the gelatin had already disappeared from the circulation in the first 10 minutes after infusion. There was a relatively rapid decrease of the plasma concentration, which was accompanied by a substantial decrease in plasma volume in the period from t=20 to t=60 min (see FIG. 2). The results indicate a very rapid dissapearance from the circulation, more than 50% disappeared within one hour and the plasma volume expanding effect lasts less than 20 minutes (FIG. 2). High gelatin concentrations were present in the urine, suggesting that the kidney excretion is a major clearance mechanism.

These results show that immediately after intravenous administration, Biogel-I distributed into the plasma compartment. The benefit of the invention plasma expander is shown since. In contrast to Gelifundol, it was not excreted into the urine. The plasma half-life is 1 tot 2 hours in the rat model. The effective period of volume expansion is thereby shorter than that of albumin, but much longer than that of Gelifundol.

The invention claimed is:

1. A composition suitable as a substitute for plasma comprising a solution of saline in a physiologically acceptable concentration and a protein having a colloid osmotic function wherein the protein having a colloid osmotic function is a recombinant gelatin-like protein consisting essentially of repeats of Gly-Xaa-Yaa triplets and comprising a molecular weight of between 10,000 and 80,000 Daltons and at least one stretch of at least 30 consecutive Gly-Xaa-Yaa triplets, wherein at least 5% of the total number of protein amino acid residues in the gelatin-like protein are proline residues, wherein the gelatin-like protein is free from globular domains and does not comprise stretches of more than 20 amino acids without a proline residue wherein less than 2% of the amino acid residues, optionally less than 1%, in the gelatin-like protein are hydroxyproline residues and wherein said recombinant gelatin-like protein is present in the range of from 2 percent to 8 percent by weight of the composition.

2. A composition according to claim 1 in which the gelatin-like protein is free of hydroxyproline residues.

3. A composition according to claim 1 in which less than 0.2%, optionally less than 0.1%, of the amino acid residues in the gelatin-like protein are hydroxylysine residues.

4. A composition according to claim 1 in which the recombinant gelatin-like protein is free of hydroxylysine.

5. A composition according to claim 1 in which less than 2%, optionally less than 1%, of the amino acid residues in the gelatin-like protein are lysine residues.

6. A composition according to claim 1 in which the recombinant gelatin-like protein is free of lysine.

7. A composition according to claim 1 in which the recombinant gelatin-like protein has a molecular weight between about 30,000 Daltons and 80,000 Daltons.

8. A composition according to claim 1 in which the recombinant gelatin-like protein is homodisperse.

9. A composition according to claim 1 which comprises one or more components in a physiologically acceptable concentration selected from $Mg^+$, $K^+$, $Ca^{2+}$, $HPO_4^{2-}$, $H_2PO_{4-}$ and glucose.

10. A composition according to claim 1 which comprises a buffering compound, optionally selected from the group consisting of $HCO_3$ and lactate $HCO_{3-}$.

11. A method of making a plasma expander composition wherein a recombinant gelatin-like protein is present in the range of from 2 percent to 8 percent by weight of the composition, the method comprising adding to a saline solution a recombinant gelatin-like protein consisting essentially of repeats of Gly-Xaa-Yaa triplets and comprising a molecular weight of between 10,000 and 80,000 Daltons and at least one stretch of at least 30 consecutive Gly-Xaa-Yaa triplets, wherein at least 5% of the total number of protein amino acid residues in the gelatin-like protein are proline residues, wherein the gelatin-like protein is free from globular domains and does not comprise stretches of more than 20 amino acids without a proline residue and wherein less than 2% of the amino acid residues in the gelatin-like protein are hydroxyproline residues.

12. A method according to claim 11 in which less than 0.2% of the amino acid residues in the gelatin-like protein are free of hydroxylysine residues.

13. A method according to claim 11 in which less than 2% of the amino acid residues of the gelatin-like protein are lysine residues.

14. Composition according to claim 1 in which less than 0.1% of the amino acid residues in the gelatin-like protein are hydroxylysine residues or lysine residues.

15. Composition according to claim 1 in which the recombinant gelatin-like protein has a molecular weight of from about 30,000 Daltons to about 80,000 Dalton and is homodisperse and which comprises one or more components in a physiologically acceptable concentration selected from $Mg^{2+}$, $K^+$, $Ca^{2+}$, $HPO_4^{2-}$, $H_2PO_4^-$ and glucose.

16. A composition suitable as a substitute for plasma comprising a solution of saline in a physiologically acceptable concentration and a protein having a colloid osmotic function wherein the protein is selected from the group consisting of Biogel I, Biogel II and Biogel III and wherein the protein is present in the range of from 2 percent to 8 percent by weight of the composition.

17. A method of making a plasma expander composition comprising adding to a saline solution from 2 percent to 8 percent by weight of the composition of a protein selected from the group consisting of Biogel I, Biogel II and Biogel III.

18. A composition according to claim 8 wherein the recombinant gelatin-like protein comprises two or more proteins each being homodisperse, the two or more proteins having different molecular weights.

19. A composition according to claim 1 comprising a pharmaceutically active compound covalently attached to the recombinant gelatin-like protein.

20. A composition according to claim 19 wherein the pharmaceutically active compound is selected from the group consisting of compounds for controlling blood clotting, vasodilatation, erythrocyte function, thrombocytes functions, leukocyte function, thrombosis, immunoresponse, blood levels of messenger molecules, blood level of hormones, heparin, beta-blockers, blood pressure regulators, angiotensin antagonists and antibiotics.

* * * * *

SEQUENCE LISTING

<160> NUMBER OF SEQ ID NOS: 13

<210> SEQ ID NO 1
<211> LENGTH: 26
<212> TYPE: DNA
<213> ORGANISM: Artificial sequence
<220> FEATURE:
<223> OTHER INFORMATION: primer HLP-PA-FW

<400> SEQUENCE: 1
gcgctcgaga aagagaggc tgaagc                                        26

<210> SEQ ID NO 2
<211> LENGTH: 108
<212> TYPE: DNA
<213> ORGANISM: Artificial sequence
<220> FEATURE:
<223> OTHER INFORMATION: primer OVL-PA-FW

<400> SEQUENCE: 2
gcgctcgaga aagagaggc tgaagctggt ccacccggtg agccaggtaa cccaggatct    60
cctggtaacc aaggacagcc cggtaacaag ggttctccag gtaatcca               108

<210> SEQ ID NO 3
<211> LENGTH: 110
<212> TYPE: DNA
<213> ORGANISM: Artificial sequence
<220> FEATURE:
<223> OTHER INFORMATION: primer OVL-PA-RV

<400> SEQUENCE: 3
tgagaacctt gtggaccgtt ggaacctggc tcaccaggtt gtccgttctg accaggttga   60
ccaggttgac cttcgtttcc tggttgacct ggattacctg gagaaccctt             110

<210> SEQ ID NO 4
<211> LENGTH: 24
<212> TYPE: DNA
<213> ORGANISM: Artificial sequence
<220> FEATURE:
<223> OTHER INFORMATION: primer HLP-PA-RV

<400> SEQUENCE: 4
tgagaacctt gtggaccgtt ggaa                                         24

<210> SEQ ID NO 5
<211> LENGTH: 24
<212> TYPE: DNA
<213> ORGANISM: Artificial sequence
<220> FEATURE:
<223> OTHER INFORMATION: primer HLP-PB-FW

<400> SEQUENCE: 5
ttccaacggt ccacaaggtt ctca                                         24

<210> SEQ ID NO 6
<211> LENGTH: 115
<212> TYPE: DNA
<213> ORGANISM: Artificial sequence
<220> FEATURE:
<223> OTHER INFORMATION: primer OVL-PB-FW

<400> SEQUENCE: 6
ttccaacggt ccacaaggtt ctcagggtaa ccctggaaag aatggtcaac ctggatcccc   60
aggttcacaa ggctctccag gtaaccaagg ttcccctggt cagccaggta accct       115

<210> SEQ ID NO 7
<211> LENGTH: 108
<212> TYPE: DNA
<213> ORGANISM: Artificial sequence
<220> FEATURE:
<223> OTHER INFORMATION: primer OVL-PB-RV

<400> SEQUENCE: 7
gcgtctgcag tacgaattct attagccacc ggctggaccc tggtttcctg gtttaccttg       60
ttcacctggt tgaccagggt tacctggctg accaggggaa ccttggtt                   108

<210> SEQ ID NO 8
<211> LENGTH: 26
<212> TYPE: DNA
<213> ORGANISM: Artificial sequence
<220> FEATURE:
<223> OTHER INFORMATION: primer HLP-PB-RV

<400> SEQUENCE: 8
gcgtctgcag tacgaattct attagc                                           26

<210> SEQ ID NO 9
<211> LENGTH: 18
<212> TYPE: DNA
<213> ORGANISM: Artificial sequence
<220> FEATURE:
<223> OTHER INFORMATION: primer HLP-H-FW

<400> SEQUENCE: 9
ccacccggtg agccagga                                                    18

<210> SEQ ID NO 10
<211> LENGTH: 102
<212> TYPE: DNA
<213> ORGANISM: Artificial sequence
<220> FEATURE:
<223> OTHER INFORMATION: primer OVL-H-FW

<400> SEQUENCE: 10
ccacccggtg agccaggaaa ccctggtcac cacggtaacc aaggacagcc aggtaacgaa       60
ggtcaaccag gtcaggaagg taatcctgga aacgagggtc at                        102

<210> SEQ ID NO 11
<211> LENGTH: 102
<212> TYPE: DNA
<213> ORGANISM: Artificial sequence
<220> FEATURE:
<223> OTHER INFORMATION: primer OVL-H-RV

<400> SEQUENCE: 11
gccaccggct ggaccttggt taccgtggtg tccctgctca ccaggttgac ctggttgacc       60
ctcgtttcca ggttgaccgt gatgaccctc gtttccagga tt                        102

<210> SEQ ID NO 12
<211> LENGTH: 18
<212> TYPE: DNA
<213> ORGANISM: Artificial sequence
<220> FEATURE:
<223> OTHER INFORMATION: primer HLP-H-RV

<400> SEQUENCE: 12

-continued

```
gccaccggct ggaccttg                                              18

<210> SEQ ID NO 13
<211> LENGTH: 161
<212> TYPE: PRT
<213> ORGANISM: Artificial sequence
<220> FEATURE:
<223> OTHER INFORMATION: Biogel II

<400> SEQUENCE: 13

Gly Pro Pro Gly Glu Pro Gly Asn Pro Gly Ser Pro Gly Asn Gln Gly
1               5                   10                  15

Gln Pro Gly Asn Lys Gly Ser Pro Gly Asn Pro Gly Gln Pro Gly Asn
            20                  25                  30

Glu Gly Gln Pro Gly Gln Pro Gly Gln Asn Gly Gln Pro Gly Glu Pro
        35                  40                  45

Gly Ser Asn Gly Pro Gln Gly Ser Gln Gly Asn Pro Gly Lys Asn Gly
    50                  55                  60

Gln Pro Gly Ser Pro Gly Ser Gln Gly Ser Pro Gly Asn Gln Gly Ser
65                  70                  75                  80

Pro Gly Gln Pro Gly Asn Pro Gly Gln Pro Gly Glu Gln Gly Lys Pro
                85                  90                  95

Gly Asn Gln Gly Pro Ala Gly Glu Pro Gly Asn Pro Gly His His Gly
            100                 105                 110

Asn Gln Gly Gln Pro Gly Asn Glu Gly Gln Pro Gly Gln Glu Gly Asn
        115                 120                 125

Pro Gly Asn Glu Gly His His Gly Gln Pro Gly Asn Glu Gly Gln Pro
    130                 135                 140

Gly Gln Pro Gly Glu Gln Gly His His Gly Asn Gln Gly Pro Ala Gly
145                 150                 155                 160

Gly
```